US012295592B2

(12) United States Patent
Paulos

(10) Patent No.: US 12,295,592 B2
(45) Date of Patent: May 13, 2025

(54) TISSUE MICROFRACTURE APPARATUS AND METHODS OF USE

(71) Applicant: THE LONNIE AND SHANNON PAULOS TRUST (AS AMENDED AND RESTATED) F/K/A THE JAMES DI, Salt Lake City, UT (US)

(72) Inventor: Lonnie E. Paulos, Pensacola Beach, FL (US)

(73) Assignee: THE LONNIE AND SHANNON PAULOS TRUST (AS AMENDED AND RESTATED) F/K/A THE JAMES DIZIKIS TRUST, DATED FEBRUARY 26, 2008, Salt Lake City, UT (US)

( * ) Notice: Subject to any disclaimer, the term of this patent is extended or adjusted under 35 U.S.C. 154(b) by 0 days.

(21) Appl. No.: 18/481,684

(22) Filed: Oct. 5, 2023

(65) Prior Publication Data

US 2024/0138851 A1 May 2, 2024

Related U.S. Application Data

(63) Continuation of application No. 17/305,532, filed on Jul. 9, 2021, now Pat. No. 11,812,975, which is a
(Continued)

(51) Int. Cl.
*A61B 17/16* (2006.01)
*A61B 90/00* (2016.01)

(52) U.S. Cl.
CPC .... *A61B 17/1604* (2013.01); *A61B 2090/034* (2016.02)

(58) Field of Classification Search
CPC . A61B 17/16; A61B 17/1633; A61B 17/1644; A61B 17/1675; A61B 17/1604;
(Continued)

(56) References Cited

U.S. PATENT DOCUMENTS

2004/0147932 A1* 7/2004 Burkinshaw ....... A61B 17/1675
606/79
2004/0153074 A1* 8/2004 Bojarski ............ A61B 17/0401
606/232
(Continued)

*Primary Examiner* — Tuan V Nguyen
(74) *Attorney, Agent, or Firm* — GOODWIN PROCTER LLP

(57) ABSTRACT

A tissue microfracture apparatus including a housing having a proximal end and a distal end that includes an aperture. The apparatus also includes an elongated member having proximal and distal ends with at least one tissue microfracture spike protruding from the distal end. The member operates cooperatively with the housing to expose a portion of the spike through the aperture. The apparatus also includes a disposing facility between the elongated member and the housing to dispose the spike in a home position within the housing. The disposing facility may be a spring element positioned at either the proximal or distal end of the housing. The elongated member may include a force receiving surface on the proximal end for receiving a force that facilitates exposing the portion of the spike. An exposure limiting facility limits the exposed portion of the spike.

10 Claims, 9 Drawing Sheets

Related U.S. Application Data continuation of application No. 16/203,443, filed on Nov. 28, 2018, now Pat. No. 11,058,434, which is a continuation of application No. 12/937,397, filed as application No. PCT/US2009/040581 on Apr. 14, 2009, now Pat. No. 10,172,626.

(60) Provisional application No. 61/045,144, filed on Apr. 15, 2008.

(58) Field of Classification Search
CPC ............. A61B 5/15113; A61B 5/15111; A61B 5/15107; A61B 5/15142
See application file for complete search history.

(56) References Cited

U.S. PATENT DOCUMENTS

| | | | | |
|---|---|---|---|---|
| 2004/0249405 A1* | 12/2004 | Watanabe | .......... | A61B 5/15194 606/181 |
| 2010/0191195 A1* | 7/2010 | Kirschenbaum | ... | A61B 17/1604 604/272 |

* cited by examiner

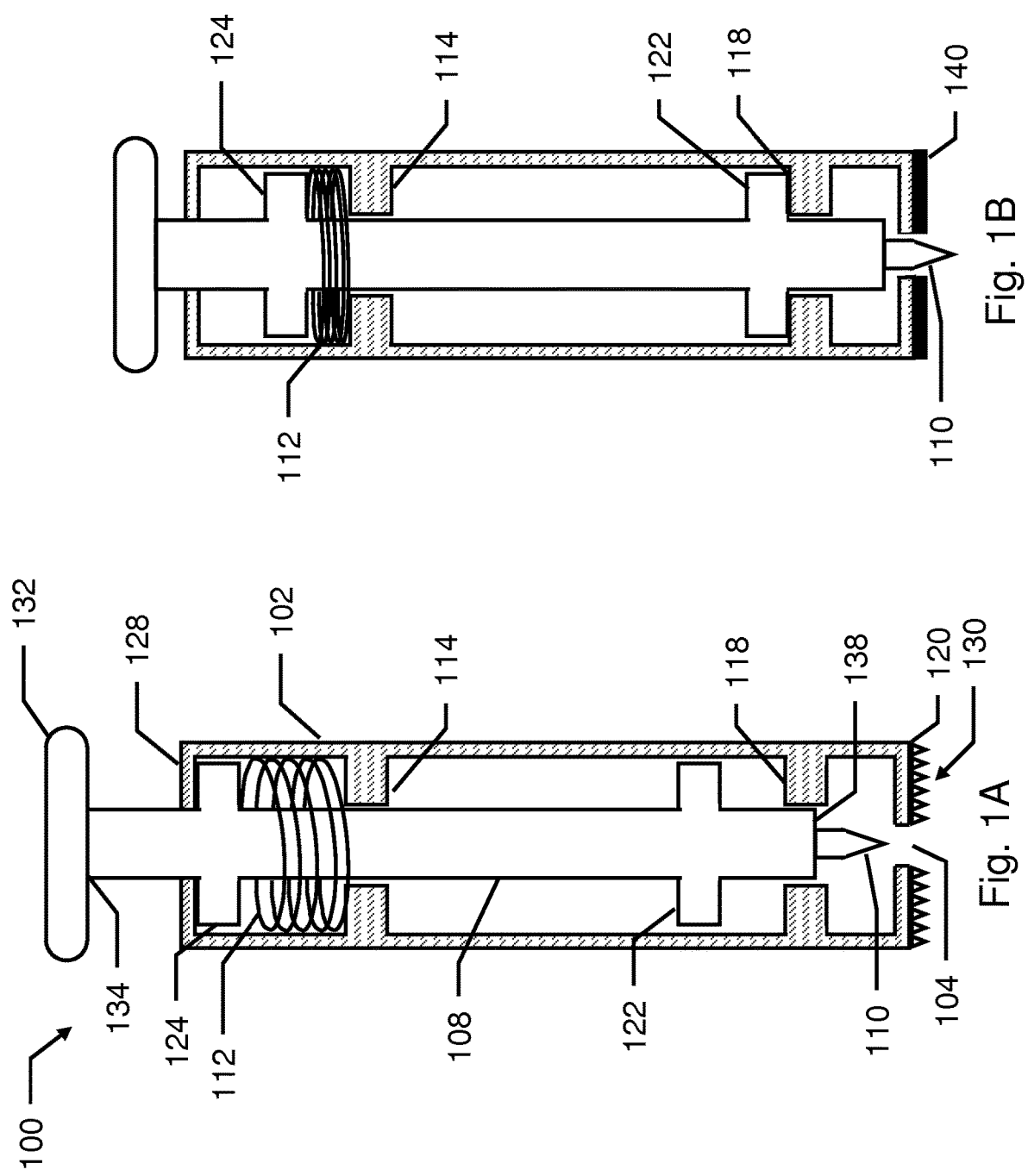

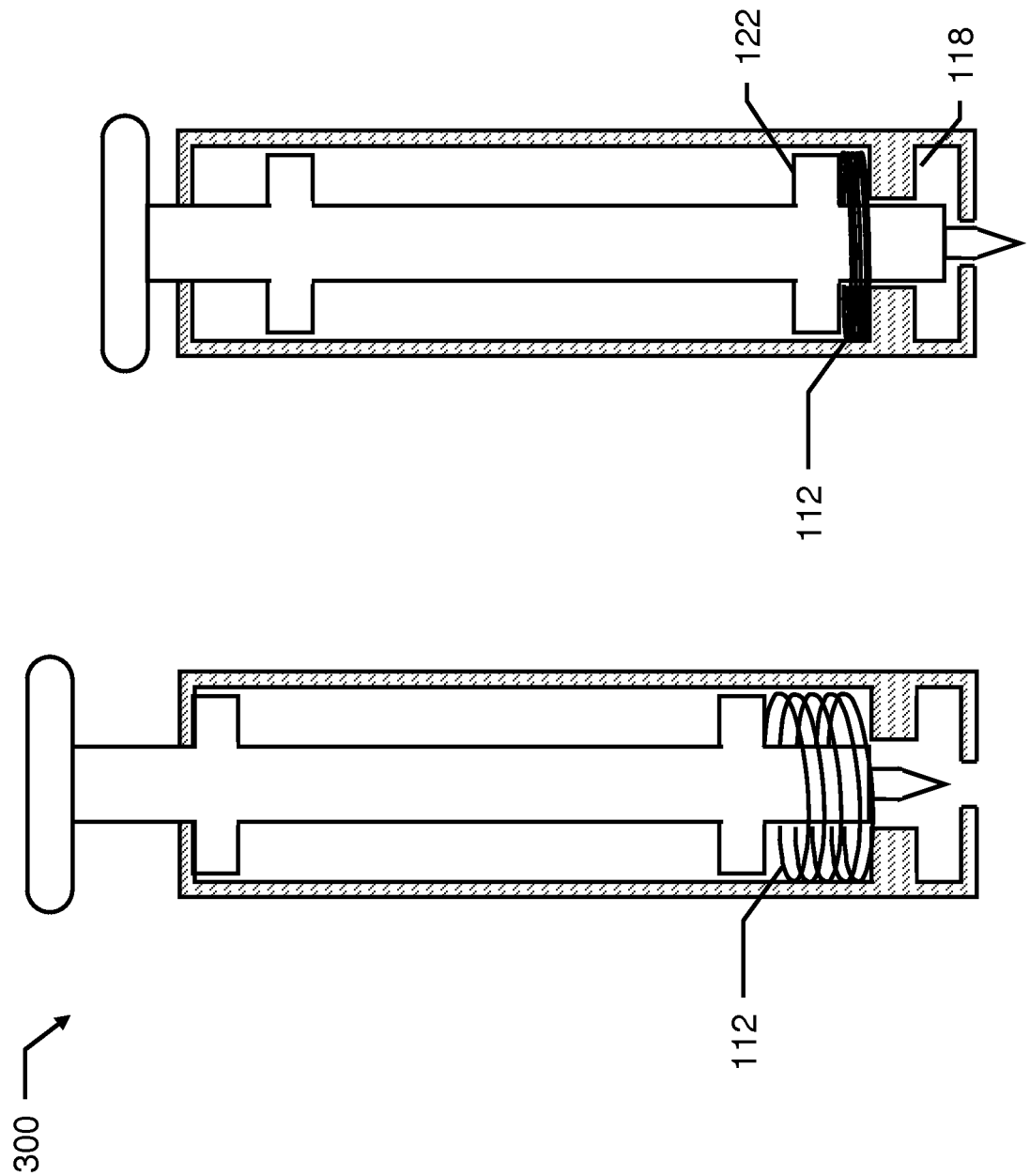

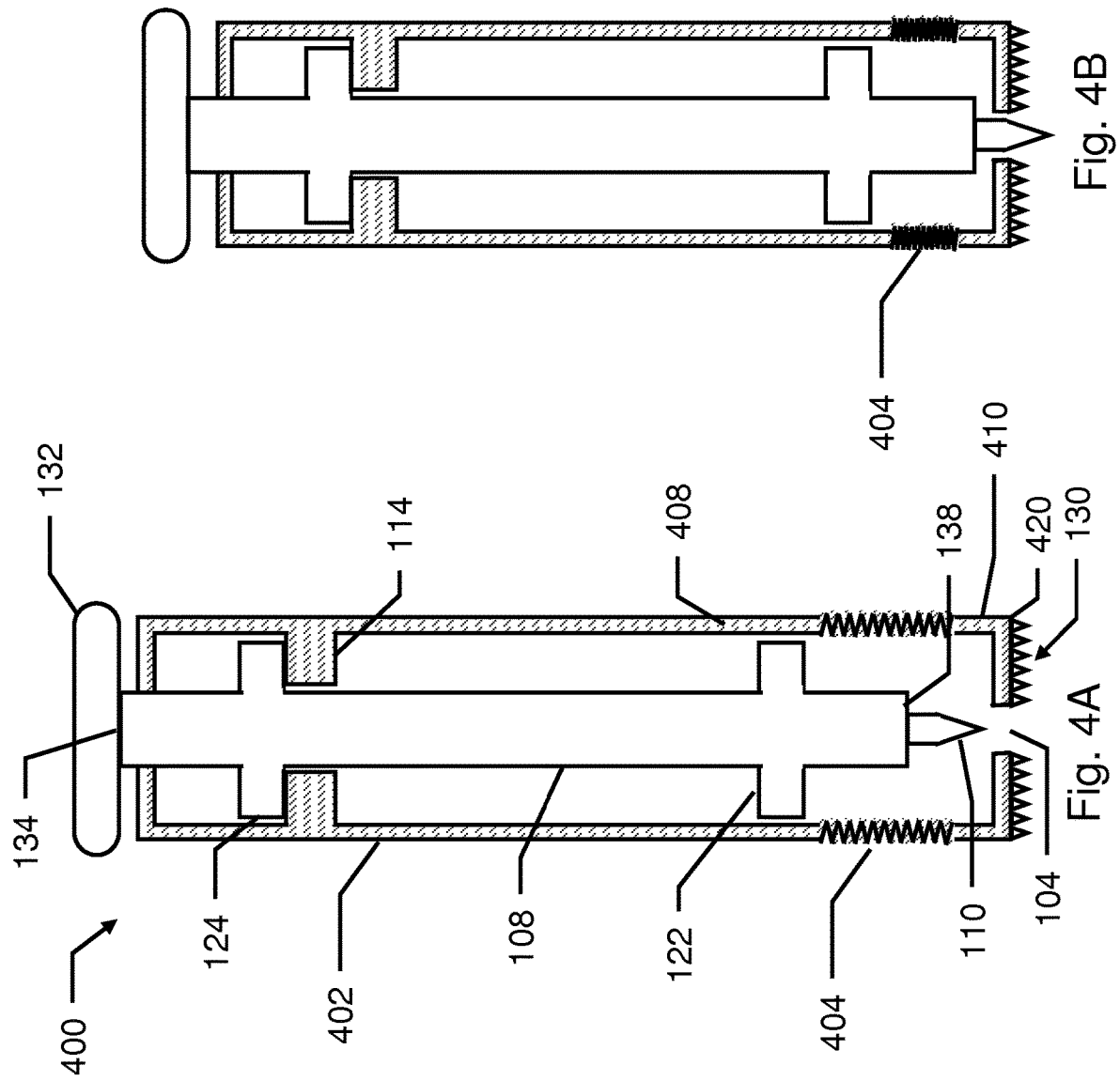

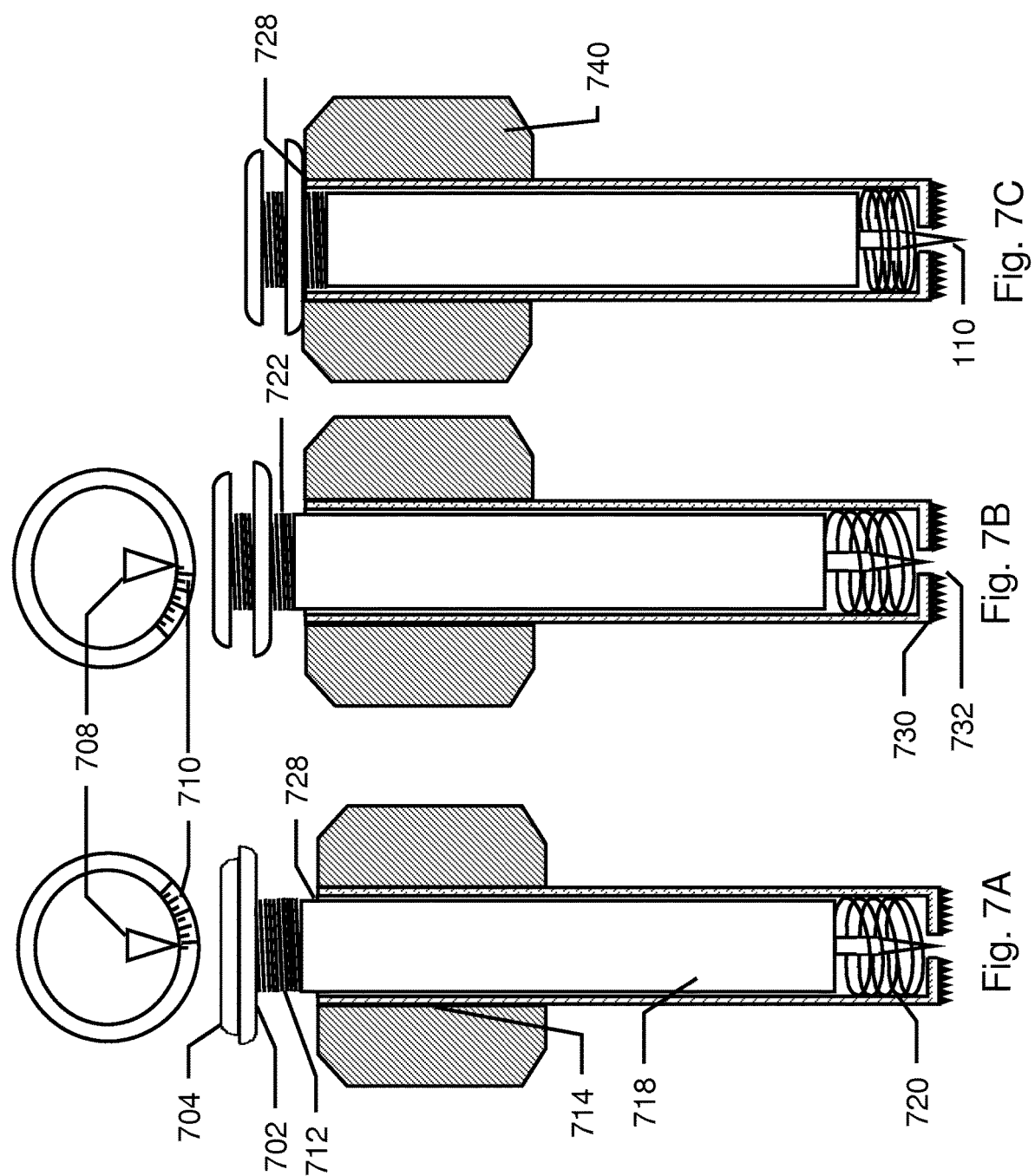

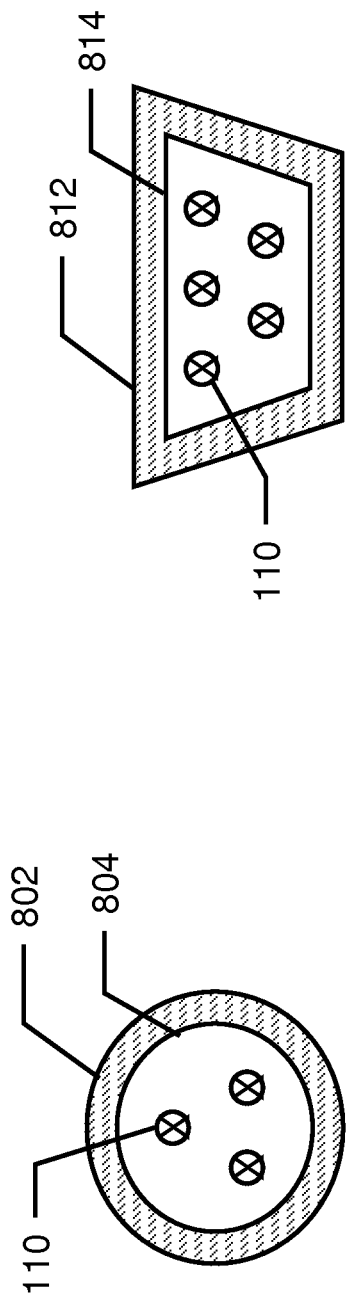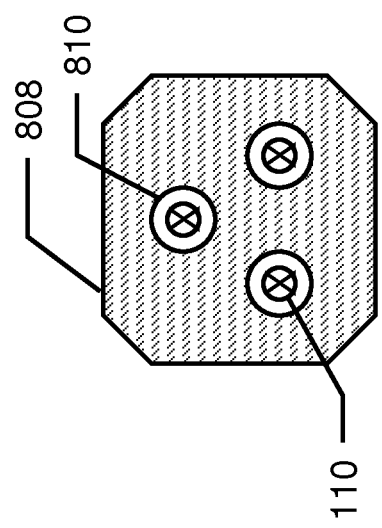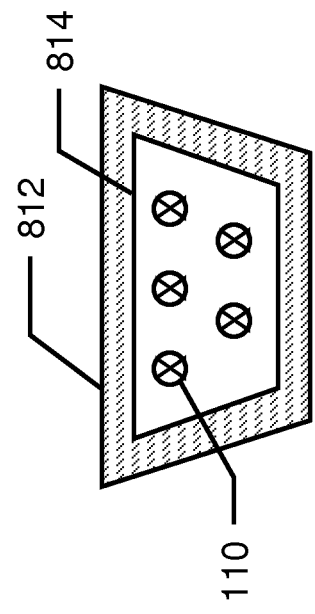
Fig. 8C
Fig. 8B
Fig. 8A

TISSUE MICROFRACTURE APPARATUS AND METHODS OF USE

CROSS-REFERENCE TO RELATED APPLICATIONS

This application is continuation of U.S. patent application Ser. No. 17/305,532, filed Jul. 9, 2021, which is a continuation of U.S. patent application Ser. No. 16/203,443, filed Nov. 28, 2018, now U.S. Pat. No. 11,058,434, which is a continuation of U.S. patent application Ser. No. 12/937,397, filed Oct. 12, 2010, now U.S. Pat. No. 10,172,626, which is a national phase application under 35 U.S.C. § 371 of International Application No. PCT/US2009/040581, filed Apr. 14, 2009, which claims the benefit of priority to U.S. Provisional Patent Application Ser. No. 61/045,144 filed on Apr. 15, 2008 which was entitled "RETRACTABLE SAFETY BONE PICK AND METHODS OF USE", the entire contents of each of which are hereby incorporated by reference in their entirety.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC APPENDIX

Not Applicable

BACKGROUND

Field

The methods and systems herein relate to orthopedic surgical techniques and in particular to the field of tissue microfracture.

Description of Related Art

Microfracture techniques are used to induce tissue repair or fibrocartilage repair of cartilage defects in articular surfaces. A surgeon may practice microfracture techniques with a sharp tipped tissue pick tool used to impact a tissue or bone. To repair bone, surgeons generally pass the sharp tipped tissue pick tool through a surgical portal made in soft tissue to reach a bone. The sharp tipped tissue pick tool can badly damage articular surfaces during this process. Also, when a sharp tipped tissue pick is presented to the bone at an angle and then struck with a mallet it can slide on the bone creating undesirable groves in the bone surface rather than producing surgically advantageous micro fractures.

U.S. Patent Publication No. 2006/0235419 A1 to Steinwachs et. al., filed Mar. 3, 2006 entitled "Medical Instrument for Performing Microfracturing in a Bone", which is herein incorporated by reference in its entirety, discloses an instrument to perform bone microfracture in a bone.

SUMMARY

In an aspect of the invention, methods and systems include a tissue microfracture apparatus that includes a housing having proximal and distal ends, the distal end including an aperture; an elongated member having proximal and distal ends with at least one tissue microfracture spike protruding from the distal end, the member operating cooperatively with the housing to expose a portion of the at least one spike through the aperture; and a disposing facility between the elongated member and the housing to dispose the at least one spike in a home position within the housing. In the aspect, the disposing facility is positioned at the proximal end of the housing. The disposing facility is positioned at the distal end of the housing. The disposing facility can comprise a resilient element such as a spring. The aspect further includes a force-receiving surface coupled to the proximal end of the elongated member for receiving a force that facilitates exposing the portion of the at least one spike. The apparatus further includes an exposure limiting facility to limit the exposed portion of the at least one spike.

In another aspect of the invention, methods and systems include a tissue microfracture apparatus that includes a housing having proximal and distal ends, the distal end including an aperture; an elongated member having proximal and distal ends with at least one tissue microfracture spike protruding from the distal end, the member operating cooperatively with the housing to expose a portion of the at least one spike through the aperture; and an exposure limiting facility to limit the exposed portion of the at least one spike. In the aspect, the exposure limiting facility can be positioned at the proximal end of the housing or at the distal end of the housing. The exposure limiting facility may comprise a resilient element such as a spring. In the aspect, the apparatus further includes a force-receiving element coupled to the proximal end of the elongated member for receiving a force that facilitates exposing the portion of the at least one spike. In the aspect, the apparatus further comprises a disposing facility between the elongated member and the housing to dispose the at least one spike in a home position within the housing.

In yet another aspect of the invention, methods and systems include a method of tissue microfracture that includes receiving a force on a force-receiving surface of a tissue microfracture apparatus thereby causing a portion of a spike to protrude through an aperture in an operative end of the apparatus and retracting the spike through the aperture. In the aspect, receiving a force on the head portion of the tissue microfracture apparatus further includes increasing a retraction force from an initial value, and retracting the spike through the aperture comprises reducing the retraction force to the initial value. The portion of the spike to protrude through the aperture can be limited independent of the retraction force. The retraction force can be provided by a disposing facility that is positioned at a proximal end of the apparatus or at a distal end of the apparatus. In the aspect, the portion of the spike to protrude through the aperture is limited by an exposure limiting feature of the apparatus other than an exterior surface of the operative end. The exposure limiting feature can be positioned at an end of the apparatus opposite the operative end or at the operative end of the apparatus.

These and other systems, methods, objects, features, and advantages of the present invention will be apparent to those skilled in the art from the following detailed description of the preferred embodiment and the drawings. All documents mentioned herein are hereby incorporated in their entirety by reference.

BRIEF DESCRIPTION OF THE FIGURES

FIG. 1A depicts a section view of an embodiment of the present invention in one operating position.

FIG. 1B depicts a section view of the embodiment of FIG. 1A in a second operating position.

FIG. 3A depicts a section view of yet another embodiment of the present invention in one operating position.

FIG. 3B depicts a section view of the embodiment of FIG. 3A in a second operating position.

FIG. 4A depicts a section view of a collapsible embodiment of the present invention in one operating position.

FIG. 4B depicts a section view of the embodiment of FIG. 4A in a second operating position.

FIGS. 7A-7C depict section views of an embodiment of the present invention with an adjustable exposure limiting facility.

FIGS. 8A-8C depict distal end views of various embodiments of the present invention.

DETAILED DESCRIPTION

Figure 2A:
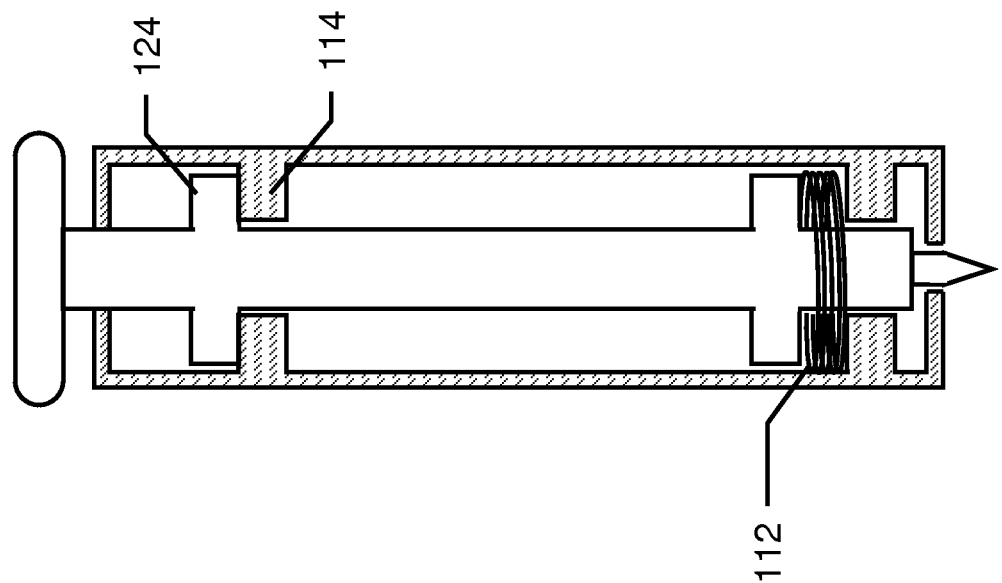
FIG. 2A depicts a section view of an alternate embodiment of the present invention in one operating position.

A tissue microfracture apparatus may be configured with features that significantly improve the safety and accuracy of such microfracture procedures while improving the quality, repeatability, and overall results. Features such as spike retractability, recessed surgical spike(s), penetration limiting, impact absorption, position stabilizers, and the like make delicate surgical procedures, such as tissue and bone microfracture, easier and therefore may improve the outcome of the procedure and recovery of the patient.

One Embodiment of the Tissue Microfracture Apparatus:

One embodiment of a tissue microfracture apparatus comprises a housing having a proximal end and a distal end that includes an aperture. The apparatus also includes an elongated member having proximal and distal ends with at least one tissue microfracture spike protruding from the distal end. The member operates cooperatively with the housing to expose a portion of the spike through the aperture. Some embodiments of the apparatus also include a disposing facility that engages the elongated member and the housing to dispose the spike in a home position within the housing. The elongated member may include a force-receiving element on the proximal end for receiving a force that facilitates exposing the portion of the spike. Some embodiments of the apparatus may also include an exposure limiting facility that limits the exposed portion of the spike.

As shown in FIG. 1A, one embodiment of the tissue microfracture apparatus 100 may include a sheath or housing 102, an elongated member 108, a force-receiving surface 132, a disposing facility 112 and at least one spike 110. The apparatus 100 includes a housing 102 having a portion to engage the rod member and an operative or distal end 120 that may include at least one aperture 104. The operative end 120 may have a rough exterior surface 130 (e.g. teeth) to facilitate positioning the apparatus 100 on a surface, such as bone. The housing 102 has a portion to support smooth operation of an elongated member 108 with a distal end 138 that may support at least one spike 110. The elongated member 108 may also have a proximal end 134 that may extend through an opening in a proximal end 128 of the housing 102. A force-receiving surface 132 or cap may be securely positioned at the elongated member proximal end 134. A disposing facility 112 may be positioned between an upper elongated member guide element 124 and a housing upper guide element 114. The elongated member 108 may be positioned in a sliding relationship to the housing upper guide element 114 and to a housing lower guide element 118. The elongated member 108 may include a lower guide element 122 positioned between the housing upper guide element 114 and the housing lower guide element 118.

The microfracture apparatus disclosed can be of any shape appropriate for use with both bone and tissue microfracture. For illustration only, for the embodiment shown in FIGS. 1A and 1B, the shape is appropriate for use with arthroscopic surgery, having a length in the range of about 4 to 18 inches, a generally cylindrical housing with a distal end diameter of about 3 to 15 millimeters (mm). The proximal end may further include a handle portion (e.g. element 740 in FIG. 7C), typically having an enlarged radial dimension, for attachment to other surgical assemblies or for use with a surgeon holding the assembly in their hand. Embodiments of the assembly with a handle can have a general shape similar to the shape of a screwdriver. Portions of the apparatus 100 may be made of surgical quality materials, such as stainless steel, surgical plastic, composites and the like including combinations thereof.

The elongated member 108 performs the function of a force rod by transmitting a portion of a force applied to the cap 132 (if present) or elongated member proximal end 134 to the spike 110. In this way, the elongated member may connect the spike 110 to the force-receiving surface.

The spike 110 may include a sharp edge or point suitable for forcibly penetrating a surface, such as bone, soft tissue or the like. It is contemplated that embodiments of the microfracture apparatus may include replaceable spikes 110 that can be exchanged for other spikes 110. Various spike shapes, sizes, materials, finishes, and the like are contemplated and included herein. Preferably, the spike material is a hardened metal or similarly rigid surgical material.

In the embodiment of FIG. 1A, the elongated member 108 is disposed in the housing 102 by the disposing facility 112, so that the at least one spike 110 does not protrude through the aperture 104. The disposing facility 112 may be configured so that the entire spike is normally within the housing 102 at a home position until a force applied to the cap 132 forces a portion of the spike 110, including the sharp edge through the aperture 104. Embodiments of the disposing facility 112 may comprise a metal spring (e.g. steel, music wire, stainless steel, bronze and the like), resilient foam, spring disk, resilient rubber, and the like disposed between the elongated member and the housing. The disposing facility 112 may apply a force between an inner surface of the housing and the elongated member so that the elongated member is normally in a home position when no force is applied to the force-receiving surface. When a force is applied to the force-receiving surface, the disposing facility may react by increasing a retraction force that is directed to disposing the elongated member in the home position.

Although many of the embodiments discussed herein illustrate a disposing facility that is compressed when a force is applied and the facility returns the spike to a home position by counteracting that compressive force, it is contemplated that embodiments of the assembly can function properly when the disposing facility is any other resilient material that can similarly react to the force such as a spring, rubber, air bubbles or elastic in tension.

With this embodiment of FIG. 1A, the elongated member 108 operates cooperatively with the housing by sliding within the housing 102 so that a force applied to a top surface of the force receiving surface 132 may cause the disposing element 112 to resist substantial movement of the elongated member 108. The elongated member 108 is retained in a portion of the housing 102 that cooperatingly allows the member to slide in relation to other elements of the assembly and housing. When the force applied to the force receiving surface 132 is sufficient to overcome the disposing element 112 resistance, the elongated member 108 may slide in the direction of the force relative to the housing 102 so that a portion of the at least one spike 110 is exposed through the aperture 104. When the force applied to the force receiving surface 132 is reduced so that it is less than the disposing element 112 resistance, the elongated member 108 may slide in a direction opposite the force thereby disposing the spike 110 within the housing 102.

Referring to FIG. 1B that depicts the apparatus 100 in an operating position with a portion of the spike 110 exposed through the aperture 104, the exposed portion may be limited by an exposure limiting facility of the apparatus. The exposure limiting facility is helpful in limiting the penetration of the spikes 110 in the microfracture procedure. Preventing excessive penetration helps prevent several undesirable results such as excessive bleeding or retarding cartilage re-growth. The exposure limiting facility comprises any cooperation of apparatus elements that can limit the exposure of spikes from the apparatus into a tissue. For example, and not for limitation, the exposure limiting facility shown in FIGS. 1A and 1B comprises exposure limiting elements that include a first exposure limiting element on the housing (e.g. housing lower guide element 118) and a second exposure limiting element on the elongated member (e.g. the elongated member lower guide element 122). The elongated member lower guide element 122 may comprise a protrusion that extends laterally outward from a sidewall of the elongated member 108. Similarly, the housing lower guide 118 may comprise a protrusion that extends laterally inward from an inner wall of the housing 102. In an example, the elongated member 108 and the housing 102 are substantially cylindrical. In this example, the lower guide 122 may be embodied as a washer shaped protrusion affixed around the elongated member 108. The housing lower guide 118 may be embodied as a washer affixed to the inner surface of the housing cylinder. As shown in FIGS. 1A and 1B, the elongated member 118 may slide along an inner edge of the housing lower guide 118 and an outer edge of the elongated member lower guide 122 may slide along an inner wall of the housing 102. The lower guide element 122 and the lower guide element 118 are shaped so that the elongated member 108 cannot pass beyond a certain point of the housing 102, thereby limiting the exposure of the spike 110 from the housing aperture 104.

In an embodiment that comprises an elongated member 108 and a housing 102 each with at least two opposing flat side walls (e.g a rectangle, an octagon, and the like), the lower guides 122 and 118 may comprise a protrusion from the at least two opposing sidewalls. Other embodiments of the exposure limiting facility may comprise buttons, nubs, or other movement restricting elements positioned to interfere when the elongated member 108 moves relative to the housing 102.

Although any length of exposure of the spikes is suitable as long as they reach the proper tissue surface, such as "bleeding bone", preferable exposure lengths for microfracture use are in the range of about 1 to 4 mm or more preferably 2 mm.

The exposure limiting facility of the apparatus can also ensure that the elongated member distal end 138 does not contact the surface of the item (e.g. tissue) that receives the at least one spike 110. In this way the portion of the surface surrounding the penetration point(s) of the at least one spike 110 is not directly impacted by the force applied to the force receiving surface 132 that causes the at least one spike 110 to penetrate the surface. This provides the benefit of virtually eliminating undesirable damage to the surface surrounding the at least one spike 110. In the embodiment of FIG. 1B the exposure limiting facility is provided by an interaction between the elongated member lower guide element 122 and the housing lower guide element 118.

The operative end 120 exterior surface may further include a shock absorbing material 140 that may mitigate the force applied to the surface of the bone that is contacted by the operative end 120. The shock absorbing material 140 may absorb a portion of the force transmitted from the elongated member 108 to the housing 102 as a result of the exposure limiting facility.

The housing distal end 120 or the elongated member distal end 138 may also be curved to more accurately reflect the surface shape of the tissue to be microfractured. This surface shape may be convex or concave or a complex curved surface. Alternatively, the distal end of the housing may include a conforming element that automatically adjusts to the tissue surface. In an example and without limitation, the confirming element may be a flexible material such as rubber.

FIG. 2A depicts an alternate embodiment of a tissue microfracture apparatus 200 that is similar to the embodiment of FIG. 1A. However, the embodiment of FIG. 2A differs in that the disposing element 112 is positioned between the lower guide elements 118 and 122, and the exposure limiting facility is accomplished by the interaction of the upper guide elements 124 and 114. Operation and other features of the apparatus 200 can be determined from the description of operation of the apparatus 100 depicted in FIG. 1A.

Figure 2B:
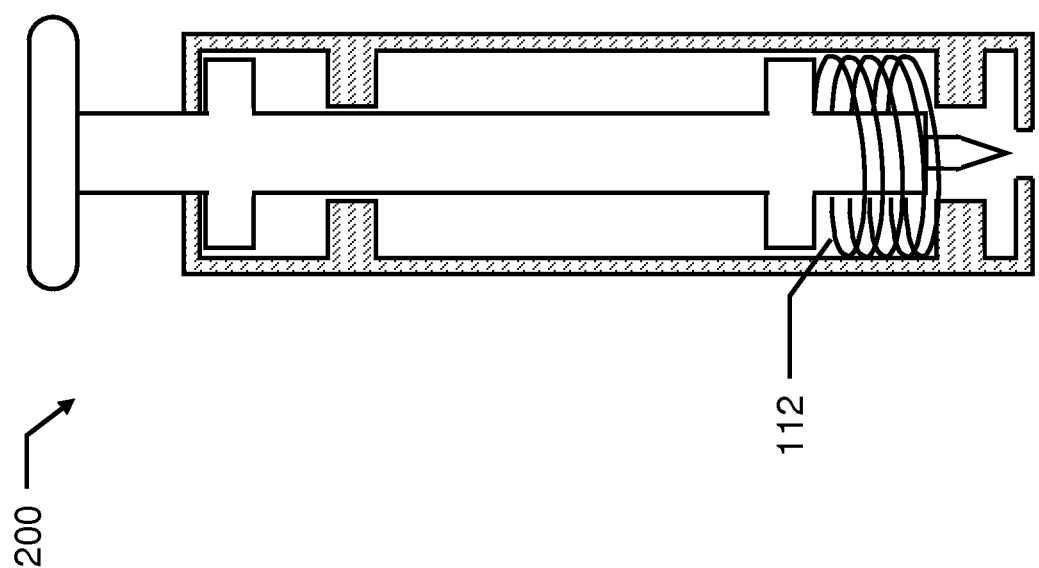
FIG. 2B depicts a section view of the embodiment of FIG. 2A in a second operating position.

FIG. 2B depicts the alternate embodiment of the retractable tissue microfracture apparatus of FIG. 2A in an exposure limited operating position. The exposure limiting facility of the apparatus ensures that the elongated member distal end 138 does not contact the surface of the item (e.g. tissue) that receives the at least one spike 110. In this way the portion of the surface surrounding the penetration point(s) of the at least one spike 110 is not directly impacted by the force applied to the cap 132 that causes the at least one spike 110 to penetrate the surface. This provides a benefit of reducing undesirable damage to the surface surrounding the at least one spike 110. In the embodiment of FIG. 2B the exposure limiting facility is provided by an interaction between the upper guide elements 124 and 114.

Limiting the exposure of the at least one spike 110 can be accomplished by the exposure limiting facilities as shown in the embodiments of FIGS. 1A, 1B, 2A, and 2B. However, there are other embodiments that can accomplish limiting spike 110 exposure. An example of one such embodiment is depicted in FIG. 3A which includes a retractable tissue microfracture apparatus 300 that is similar to the apparatus 200 depicted in FIG. 2A. However, apparatus 300 does not include the housing upper guide element 114. In all other respects, apparatus 300 may be substantially similar to apparatus 200. As depicted in FIG. 3B, which depicts the apparatus 300 in a spike 110 exposure limited operating position, exposure limiting may be provided by an interaction between the disposing element 112 and the lower guide elements 118 and 122. The exposure of a portion of the at least one spike 110 may be limited by maximum compression of disposing element 112 between the elongated member lower guide element 122 and the housing lower guide element 118.

In an alternate to the embodiments of FIGS. 2A, 2B, 3A, and 3B the housing lower guide element 118 maybe removed; thereby allowing disposing element 112 to operate between the elongated member lower guide element 122 and an interior surface of the operative end 120. The basic operation and features of such an embodiment may be substantially similar to the embodiments depicted in FIGS. 2A, 2B, 3A, and 3B.

FIG. 4A depicts an alternate embodiment of a retractable tissue microfracture apparatus 400 that may include a compressible housing or sheath, an elongated member or force rod, a force-receiving surface or cap, and a spike. Apparatus 400 may include a housing 402 having a distal end 420 that may include at least one aperture 104. The operative end 420 may have a rough surface 130 (e.g. teeth) to facilitate positioning and maintaining a position of the apparatus 400 on a surface, such as bone. The housing 402 may support smooth operation of an elongated member 108 with a distal end 138 that may support at least one spike 110. The elongated member 108 may also have a proximal end 134 that may extend through an opening in a proximal end 128 of the housing 402. A force-receiving surface such as a cap 132 may be securely positioned at the elongated member proximal end 134. A disposing facility 404 may be configured within the assembly 400. The elongated member 108 may include a lower guide element 122. The lower guide element 122 that may be positioned in a sliding relationship to an interior surface of the housing 402.

The disposing facility 404 may be a resilient compressible material which responds to a compression force by first compressing and then expanding to a pre-compression size. As discussed herein, the disposing facility may also be a resilient material that provides the same force features in tension. The disposing facility 404 may be a fabricated portion of the housing 402 or a separately fabricated facility that is attached between a main portion of the housing 408 and a lower portion of the housing 410 that may include the operative end 420.

The elongated member 108 may perform the function of a force rod by transmitting a portion of a force applied to the cap 132 or elongated member proximal end 134 to the spike 110. In this way, the elongated member may connect the spike 110 to a force-receiving surface (e.g. the cap 132).

In the embodiment of FIG. 4A, the elongated member 108 is disposed in the housing 402 by the disposing facility 404, so that the at least one spike 110 does not protrude through the aperture 104. The elongated member 108 may normally be disposed within the housing so that the elongated member upper guide element 124 rests firmly against the housing upper guide element 114. This ensures that any force applied to the cap 132 is transmitted to the housing through the upper guide elements 124 and 114. When the operative end 420 is placed against a surface, such as a bone surface, a force applied to a top surface of the force-receiving surface 132 may cause the disposing element 404 to resist movement of the elongated member 108 in the direction of the operative end 420. When the force applied to the cap 132 is sufficient to overcome the disposing element 404 resistance, the elongated member 108 and the housing main portion 408 may move in the direction of the force relative to the housing lower portion 410 that is positioned against a surface (e.g. bone). In response thereto, the disposing element 404 may compress, resulting in the at least one spike 110 being exposed through the aperture 104. When the force applied to the cap 132 is reduced so that it is less than the disposing element 404 resistance, the elongated member 108 and housing main portion 408 will move in a direction opposite the force thereby disposing the spike 110 again within the housing 402 into a home position. The housing main portion 408 may extend over disposing member 404 so that the housing main portion 408 slides over the housing lower portion 410 during operation. Alternatively, the housing lower portion 410 may extend over disposing element 404 so that the housing lower portion 410 slides over the housing main portion 408 during operation. Housing main portion 408 and lower portion 410 may freely slide relative to one another or may be interlocked to prevent the housing portions from separating when disposing element 404 fully expands.

Referring to FIG. 4B that depicts the apparatus 400 in an operating position with a portion of the spike 110 exposed through the aperture 104, the portion to be exposed may be limited by an exposure limiting facility of the apparatus. The exposure limiting facility of the apparatus ensures that the elongated member distal end 138 does not contact the surface of the item (e.g. tissue or bone) that receives the at least one spike 110. In this way the portion of the surface surrounding the penetration point(s) of the at least one spike 110 is not directly impacted by the force applied to the cap 132 that causes the at least one spike 110 to penetrate the surface. This provides the benefit of reducing, and in some embodiments virtually eliminating undesirable damage to the surface surrounding the point of impact of the at least one spike 110. In the embodiment of FIG. 4B the exposure limiting facility is provided by a maximum compression of disposing element 404.

Figure 5:
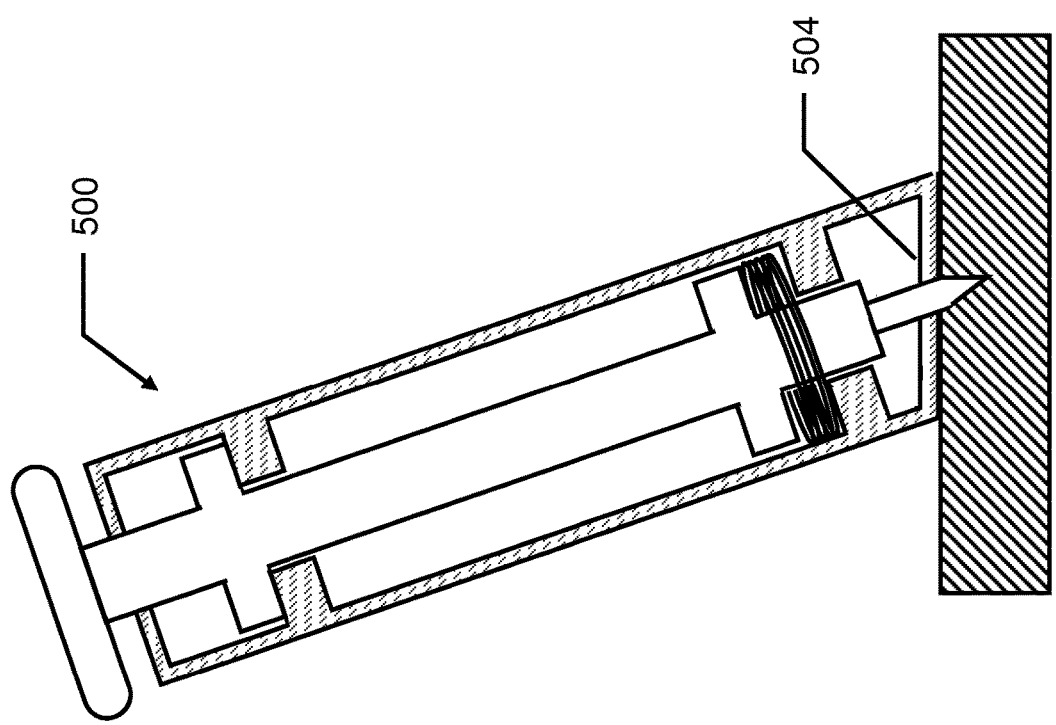
FIG. 5 depicts a section view of an angled embodiment of the present invention.

FIG. 5 depicts an embodiment of a retractable tissue microfracture apparatus 500 that is adapted to introduce an exposed spike at an odd angle relative to a surface, such as a bone surface for microfracture. The angle of introduction of the spike may depend on the angle presented by a distal end 504 of the apparatus 500. The distal end 504 may facilitate introducing a spike at an angle of 10 degrees relative to normal, 20 degrees relative to normal, and the like. Other angles are possible and embodiments to support all angles are contemplated. The apparatus 500 may include an adjustable distal end 504 that facilitates selecting an angle of spike introduction. Features and facilities such as exposure limiting, disposing the spike within the housing, surface gripping teeth, and any other feature herein disclosed may be included in an embodiment represented by apparatus 500.

Figure 6:
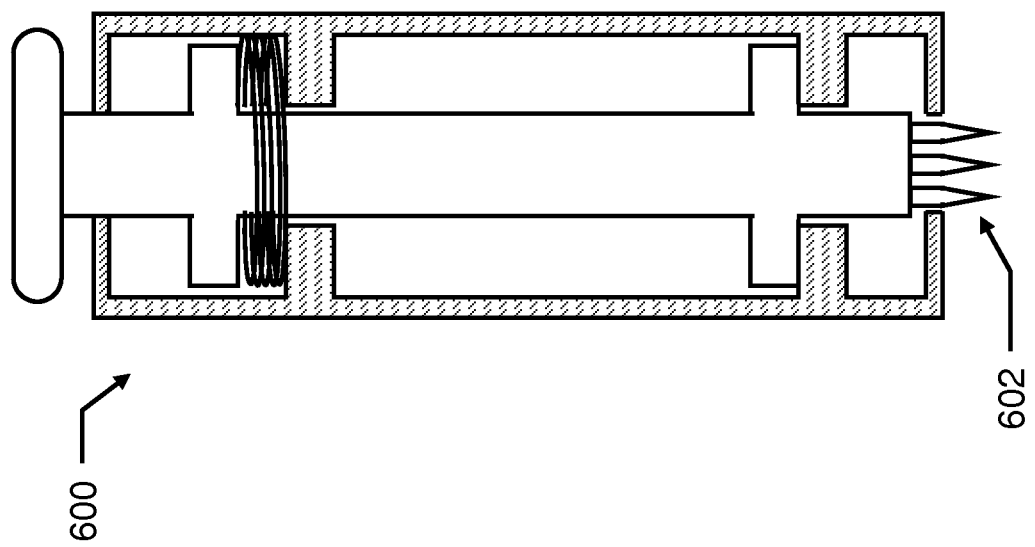
FIG. 6 depicts a section view of an embodiment of the present invention with a plurality of spikes.

FIG. 6 depicts an alternate embodiment of a retractable tissue microfracture apparatus 600 that includes a plurality of spikes 602 for effecting microfracture techniques. The apparatus 600 depicted in FIG. 6 may be described similarly to apparatus 100 depicted in FIG. 1A and FIG. 1B. However, certain aspects may be adapted (e.g. dimensions of the housing 102, elongated member 108, disposing facility 108, and the like) to support exposure of a plurality of spikes 602. In an example, the aperture 104 of apparatus 100 shown in FIG. 1A may be enlarged to support the plurality of spikes 602 depicted in FIG. 6. In another example, disposing facility 108 of FIG. 1A may provide greater resistive force to effectively retract exposed spikes from a penetrated surface such as bone.

The exposure limiting facility of the apparatus may include adjustable features that allow a surgeon to determine the depth of penetration of the spike into a bone or other tissue. The exposure limiting facility may be adjustable through a feature that allows the housing upper or lower guide elements to be repositioned along the length of the housing. In particular, embodiments can include adjustable/threaded elements that facilitate positioning the exposure limiting facility elements and may include visible marks on the apparatus to indicate exposure. The amount of exposure may also be adjusted by placing various thickness spacers between the elongated member guide elements and the housing guide elements. The amount of exposure may also be adjusted by adjusting an amount of the spike that protrudes from the distal end of the elongated member. Other methods and techniques for adjusting a spike exposure limit are contemplated and included herein.

FIGS. 7A through 7C depict an alternate embodiment of the retractable tissue microfracture apparatus with a representative embodiment of an adjustable exposure limitation facility. A portion of the spike 110 to be exposed may be adjustable so that a user, such as a surgeon, can control a protrusion depth of the spike 110 into tissue during a procedure such as a microfracture procedure. The embodiment of FIGS. 7A through 7C includes a force-receiving surface 704 mounted to an end of a threaded end 712 of an elongated member 718. The elongated member 718 may slide smoothly within a housing 714 that includes an open end 728 and a distal or operative end 730. The distal or operative end 730 may include an aperture 732 through which the spike 110 may be exposed. A disposing facility 720 may be placed between an end of the elongated member 718 that supports the spike 110 and an interior surface of the distal or operative end 730. The disposing facility 720 may facilitate positioning the elongated member 718 in a home position that results in the spike 110 being disposed within the housing 714.

An exposure limiting dial 702 may be threaded on the elongated member threaded end 712 so that it is disposed between the force-receiving surface 704 and the open housing end 728. The exposure limiting dial 702 may be mated with the threaded end 712 so that when the dial 702 is rotated, it moves toward or away from the force-receiving surface 704. As an example, rotating dial 702 clockwise will move dial 702 away from the force-receiving surface 704 and toward the housing open end 728.

Referring to FIG. 7B, the exposure limiting dial 702 can be rotated to a position to control a portion of the spike 110 to be exposed. Continuing the example of above, rotating the dial 702 counter-clockwise may allow a greater portion of the spike 110 to be exposed than rotating the dial 702 clockwise. The position to which the dial 702 is rotated along the threaded portion 712 determines the spike 110 exposure because a motion of the elongated member 718 that exposes the spike is stopped by the dial 702 butting up against housing open end 728. In particular, threaded portion 722 that is visible between the dial 702 and the housing open end 728 is representative of the portion of the spike 110 to be exposed.

FIG. 7C depicts an exposure limited operating position of the tissue microfracture apparatus wherein the elongated member 718 has been forced toward the housing operative end 730 (e.g. by a force applied to the force-receiving surface 704) and the exposure limiting dial 702 is making contact with the housing open end 728. In this operating position, the spike 110 is exposed through the aperture 732 and the disposing facility 720 is engaged to reposition the spike 110 within the housing when the force applied to the force-receiving surface 704 is removed.

Referring again to FIGS. 7A and 7B, the force-receiving surface 704 may include an index mark 708 on a top surface. The exposure limiting dial 702 may also include exposure marks 710 on a top surface that is visible on the outside of the perimeter of the force-receiving surface 704. The exposure marks 710 may include dimensions that represent exposure limits. An alignment of the index mark 708 and an exposure mark 710 may provide an indication to the surgeon that the spike 110 will be exposed by the aligned dimension. The alignment of index mark 708 and exposure mark 710 in FIG. 7A indicates a first exposure limit position of the dial 702. The alignment index mark 708 and exposure marks 710 in FIG. 7B depicts a second exposure limit position of the dial 702.

Although the above embodiment describes an adjustable exposure limiting facility comprising the interaction of threaded dials on a threaded end of the elongated member, any method of adjusting the movement of the spikes or elongated member in relation to the housing distal end is contemplated. Examples of other embodiments include but are not limited to having an adjustable protrusion of the spikes from the elongated member distal end, an adjustable cap on the distal end of the housing, having an adjustable housing guide element interact with a stationary elongated member guide element or any other means to adjustably limit the movement or exposure of the spikes relative to housing elements and the housing aperture. Other embodiments of providing marks or other calibration means reflecting the exposure of the spikes are also contemplated.

Referring to FIG. 8A through 8C, various example embodiments of a retractable tissue microfracture apparatus are presented in distal end views. Each of the embodiments of FIGS. 8A through 8C represent different apparatus shapes, spike configurations, and aperture shapes. FIG. 8A depicts a distal end view of an apparatus with a substantially round profile 802 and three spikes 110 positioned to substantially form a triangle in a single aperture 802. FIG. 8B depicts a distal end view of an apparatus with an octagon profile 808 and three spikes 110 positioned to substantially form a triangle, with each spike 110 visible through one of three dedicated apertures 810. FIG. 8C depicts a distal end view of a rectangular profile 812 and five spikes arranged in two rows visible through a single aperture 814. The embodiments depicted in FIGS. 8A through 8C are merely exemplary combinations of apparatus shape, aperture shape and quantity, and spike quantity and position. Any and all other combinations, shapes, and quantities of aperture and spikes are contemplated and included herein.

Considering the embodiments of retractable safety bone microfracture apparatus described above, at a limit of exposure provided by an exposure limiting facility, the disposing element may be resisting the force applied to the force-receiving surface. However, the disposing element may not have reached a maximum resistance when the exposure limit is achieved. By the exposure limiting facility preventing the disposing element from reaching a maximum resistance, the portion of the at least one spike being exposed through the aperture may not be limited by the disposing element. In this way, a surgeon can ensure that applying a force that is sufficient to overcome the disposing element resistance will expose the at least one spike to a length provided by the exposure limiting facility rather than to a shorter length determined by the maximum resistance of the disposing element.

It is also contemplated that the exposure limitation of the spike may be performed by limiting the amount of force applied to the force-receiving surface. If the amount of force applied to the force-receiving surface is less than the resistance force provided by the disposing facility, this point of disposing facility compression may function as the exposure limiting facility. Embodiments of this type are contemplated where the force applied to the force-receiving surface can be varied in a predictable manner. This situation may be possible if the force is applied by a trigger mechanism driven by a calibrated spring, a calibrated pneumatic driver, calibrated electric driver or similar methods of applying a variable force.

Figure 9:
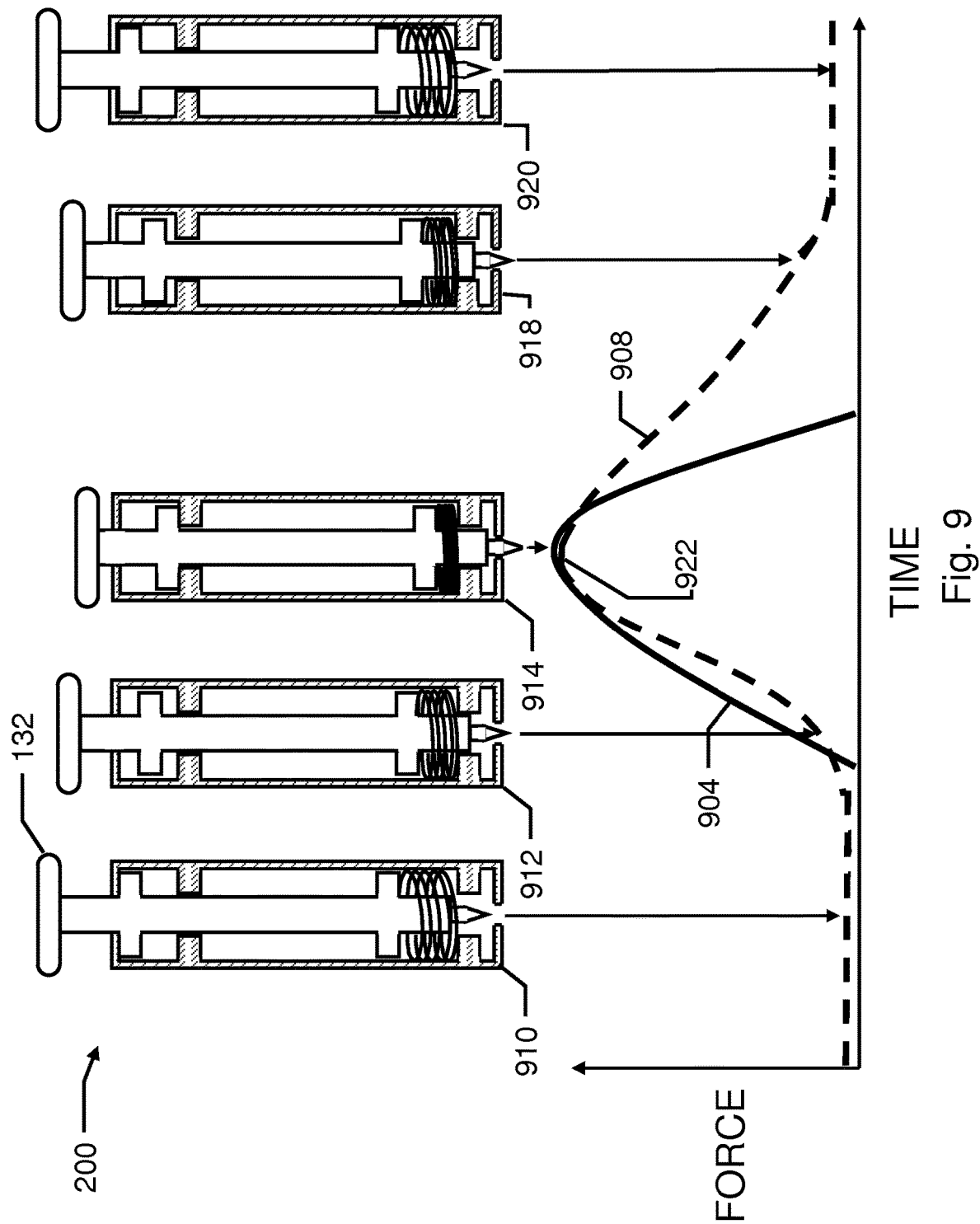
FIG. 9 depicts an operating force graph of an embodiment of the present invention.

FIG. 9 depicts a force diagram and various operating positions of a spike exposure limiting embodiment of the invention. Prior to receiving a force to affect a microfracture, the apparatus may be in a non-exposed operating position 910. A force applied to the cap 132 may be an impact such as from a surgical mallet. A representation of a force applied by a surgical mallet or the like is depicted as mallet force 904. The disposing element retraction force is depicted as retraction force 908. As the mallet force 904 is applied to the cap 132, the elongated member begins to respond by sliding within the housing as shown in apparatus operating position 912. In the operating position 912, the disposing element may begin to resist the operating force as depicted by the corresponding slight rise in the retraction force 908. Coincident with or slightly after the operating force applied to the cap 132 is maximized, the spike exposure limit may be reached as depicted in operating position 914 in which a limited portion of the spike is exposed through the aperture. The corresponding retraction force 908 levels off as depicted by the peak level 922 because the spike exposure limiting facility stops the motion of the elongated member and the excess force is transferred to the housing. With the mallet force 904 substantially removed, the disposing element proceeds to retract the spike toward the interior of the housing as depicted in apparatus operating position 918. Apparatus operating position 920 depicts the apparatus in an operating position similar to operating position 910 with the spike 110 fully disposed within the housing.

Operational Use of One Embodiment of the Microfracture Apparatus:

Generally, embodiments of methods to use the apparatus comprises receiving a force on the force-receiving surface of the elongated member which causes a portion of a spike to be exposed through an aperture in the distal end of the apparatus and the disposing facility retracts the spike into a home position within the apparatus. For illustration purposes, and not for limitation, the operational use of one embodiment of the tissue microfracture apparatus is described below as used with an arthroscopic bone microfracture procedure. It is understood that other embodiments of the apparatus, as well as other embodiment of the methods are contemplated such as, but not limited to open bone microfracture procedures as well as microfracture procedures for soft tissues.

The use of embodiments of the present invention can also accompany other microfracture procedures and techniques such as but not limited to diagnostic evaluation of the patient and the tissue as well as tissue preparation and clot formation. An example of some of these procedures are described in U.S. Pat. No. 6,960,214 to Burkinshaw, filed Jan. 21, 2003 entitled "Method for Performing Automated Microfracture" which is herein incorporated by reference in its entirety.

In one example of operation of a retractable safety bone microfracture apparatus during arthroscopic surgery, a tissue microfracture apparatus such as shown in FIG. 1A is provided. The tissue microfracture apparatus provided may be manufactured or setup in a variety of spike exposure configurations that allow a surgeon to select the apparatus that has the proper exposure in a microfracture procedure to ensure the spike reaches bleeding bone. Additionally, if the apparatus has an adjustable exposure, the surgeon can adjust the apparatus to ensure the exposure reaches bleeding bone.

At this point of the present methods, the bone under the defect has been debrided of cartilage tags by means selected by the surgeon. The tissue microfracture apparatus is inserted through a patient portal that provides access to a bone. Because the spike is disposed within the housing, the apparatus can be inserted without having the spike engage the soft tissue. Once the apparatus is inserted, the distal end of the housing is positioned against a surface to be microfractured. The rough surface of the operative end of the microfracture apparatus facilitates holding the apparatus in position on the exposed bone. The proximal end of the apparatus is outside of the portal and may be held in the surgeon's hand. The force-receiving surface or cap of the apparatus is also exposed to the surgeon.

To this point in the procedure, the disposing facility of the apparatus has disposed the spikes completely within the housing in a home position so that the spikes have not been exposed to the tissue of the patient.

With this assembly held in place by the surgeon, a mallet or other striking tool is then used to impact the force-receiving surface of the apparatus. The elongated member receives and transfers the impact force to the spikes, forcing the elongated member to advance within the housing thereby exposing the spikes through an aperture in the distal end of the housing and permitting the spikes to impact the bone. In this embodiment, the exposure limiting facility of the apparatus limits the exposure of the spikes to a predetermined distance as discussed above.

With the release of the striking force (the mallet impact is rapidly removed), the disposing facility retracts the spikes into the housing thus preventing damage to the patient tissues and articular surfaces. The surgeon can then repeat these steps to continue the microfracture. At the completion of the microfracture, the apparatus can be removed.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention. Although this invention has been described in the above forms with a certain degree of particularity, it is understood that the present disclosure has been made only by way of example and numerous changes in the details of construction and combination and arrangement of parts may be resorted to without departing from the spirit and scope of the invention. It is also understood that the methods and systems described can benefit a variety of surgical or similar procedures. Notwithstanding the specific example embodiments set forth above, all such variations and modifications that would be envisioned by one of ordinary skill in the art are intended to fall within the scope of this disclosure.

I claim:

1. An apparatus comprising:
   a cannula having a first end, a primary portion extending from the first end to a distal portion, the distal portion extending from the primary portion to a second end, and a channel extending between the first end and the second end, wherein the channel has a first transverse dimension between the first end and the second end and having a second transverse dimension at the second end that is smaller than the first transverse dimension, wherein the first transverse dimension is disposed at a point that is closer to the second end than to the first end, and wherein the distal portion is configured such that a terminal surface of the second end is disposed at an angle relative to a terminal surface of the first end; and
   a penetrator having a distal end and a first transverse dimension, the penetrator configured to be disposed in the channel of the cannula such that the penetrator is movable between a retracted position and an extended position, wherein the penetrator is configured to be moved from the retracted position to the extended position to form in subchondral bone a microfracture.

2. The apparatus of claim 1, wherein the angle of the terminal surface of the second end relative to the terminal surface of the first end is adjustable between a plurality of angles.

3. The apparatus of claim 1, wherein the angle of the terminal surface of the second end relative to the terminal surface of the first end is configured to dispose the penetrator at least partially into the subchondral bone at an angle of 10 degrees or 20 degrees.

4. The apparatus of claim 1, wherein the terminal surface of the second end comprises gripping teeth.

5. The apparatus of claim 1, wherein the cannula comprises a handle having an indicator indicative of an exposure position of the distal end of the penetrator with respect to the terminal surface of the second end.

6. The apparatus of claim 1, wherein the penetrator is configured to be manually moved from the retracted position to the extended position and where the terminal surface of the second end comprises an opening configured to receive the distal end of the penetrator.

7. The apparatus of claim 6, wherein the penetrator has an enlarged head, and wherein the enlarged head has a cylindrical shape.

8. The apparatus of claim 1, wherein the penetrator has an enlarged head, and a penetration distance is limited by the enlarged head contacting the cannula.

9. The apparatus of claim 1, wherein the distal end of the penetrator comprises a pointed tip.

10. The apparatus of claim 1 further comprising:
    a penetrator tab coupled to the penetrator and configured to enable retraction of the penetrator relative to the cannula.

* * * * *